US009108205B2

(12) United States Patent
Böttger et al.

(10) Patent No.: US 9,108,205 B2

(45) Date of Patent: Aug. 18, 2015

(54) COATING APPARATUS FOR COATING AN INSIDE OF A HOLLOW BODY WITH AN ATOMIZED FLUID

(75) Inventors: Frank Böttger, Ravensburg (DE); Günther Späth, Tettnang (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 277 days.

(21) Appl. No.: 12/999,258

(22) PCT Filed: Jun. 18, 2009

(86) PCT No.: PCT/EP2009/004386

§ 371 (c)(1), (2), (4) Date: Dec. 15, 2010

(87) PCT Pub. No.: WO2009/153040

PCT Pub. Date: Dec. 23, 2009

(65) Prior Publication Data

US 2011/0088617 A1 Apr. 21, 2011

(30) Foreign Application Priority Data

Jun. 19, 2008 (DE) ......................... 10 2008 030 272

(51) Int. Cl.

*B05B 7/04* (2006.01)
*B05B 13/06* (2006.01)

(Continued)

(52) U.S. Cl.

CPC ................ *B05B 7/0416* (2013.01); *B05B 7/04* (2013.01); *B05B 7/0475* (2013.01); *B05B 13/06* (2013.01);

(Continued)

(58) Field of Classification Search

USPC ......... 118/317, 318, 305, 306, 323, 500, 503; 239/226, 265, 398

See application file for complete search history.

(56) References Cited

U.S. PATENT DOCUMENTS 1,865,436 A * 7/1932 Ferguson ........................ 118/58
2,264,564 A * 12/1941 Connor ......................... 239/346

(Continued)

FOREIGN PATENT DOCUMENTS

DE 19509223 11/1996
DE 19509223 C1 * 11/1996

(Continued)

OTHER PUBLICATIONS

English Translation of the International Preliminary Report on Patentability according to Chapter II for PCT/EP2009/004386, issued Mar. 11, 2011 (4 pages).

(Continued)

*Primary Examiner* — Dah-Wei D Yuan
*Assistant Examiner* — Binu Thomas
(74) *Attorney, Agent, or Firm* — Harness, Dickey & Pierce, P.L.C.; Stephen T. Olson

(57) ABSTRACT

A coating device for coating an inside of a hollow body with an atomized fluid has at least one atomizing tube enclosing an atomizing channel. A pressurized propellant gas for atomizing an unatomized fluid can be introduced into the atomizing tube. The atomizing tube has at least one outlet opening and further has at least one hollow needle having a discharge opening for the unatomized fluid. The at least one hollow needle interacts with the atomizing channel and is arranged essentially coaxially thereto. The atomizing tube and the hollow needle form a Venturi arrangement.

27 Claims, 5 Drawing Sheets

Figure 1:
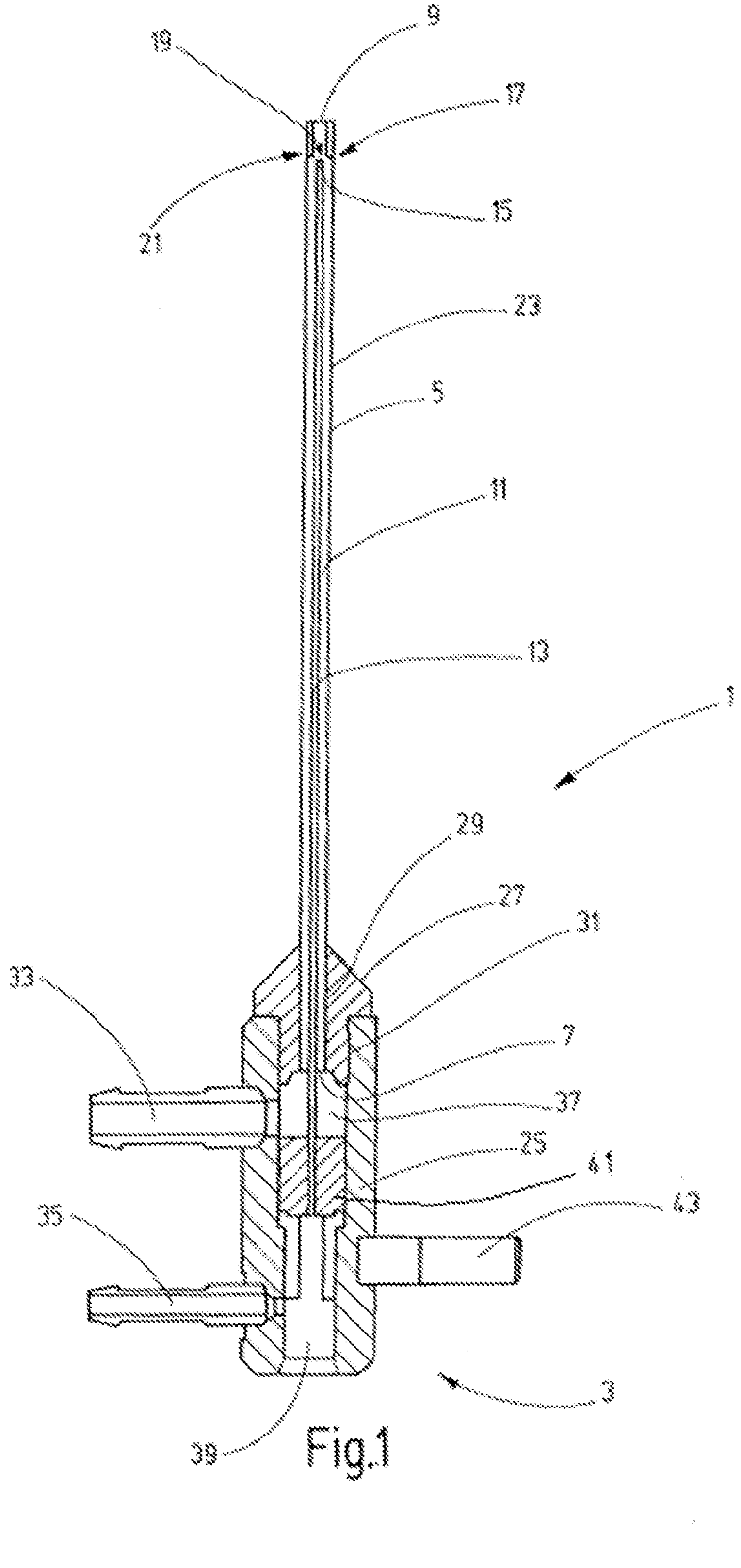

(51) Int. Cl.

| | |
|---|---|
| *B05D 7/22* | (2006.01) |
| *A61M 5/31* | (2006.01) |
| *B05C 7/08* | (2006.01) |
| *B05B 7/06* | (2006.01) |

(52) U.S. Cl.

CPC .......... *B05B 13/0627* (2013.01); *A61M 5/3129* (2013.01); *B05B 7/064* (2013.01); *B05C 7/08* (2013.01); *B05D 7/22* (2013.01)

(56) References Cited

U.S. PATENT DOCUMENTS

| | | | | | |
|---|---|---|---|---|---|
| 2,511,474 | A | | 6/1950 | Kremer | |
| 2,868,163 | A | * | 1/1959 | Boyd | 118/317 |
| 3,951,101 | A | * | 4/1976 | Karakawa et al. | 118/301 |
| 4,164,325 | A | * | 8/1979 | Watson | 239/252 |
| 4,819,878 | A | | 4/1989 | Bailey et al. | |
| 4,960,244 | A | * | 10/1990 | Maag et al. | 118/303 |
| 5,038,708 | A | * | 8/1991 | Wells et al. | 118/318 |
| 5,141,774 | A | * | 8/1992 | Prittinen et al. | 118/317 |
| 5,456,940 | A | * | 10/1995 | Funderburk | 118/317 |
| 5,738,728 | A | * | 4/1998 | Tisone | 118/305 |
| 6,722,584 | B2 | * | 4/2004 | Kay et al. | 239/594 |
| 7,143,967 | B2 | | 12/2006 | Heinrich et al. | |
| 2005/0126478 | A1 | * | 6/2005 | Donatti et al. | 118/317 |
| 2008/0280025 | A1 | | 11/2008 | Scheer | |

FOREIGN PATENT DOCUMENTS

| | | | |
|---|---|---|---|
| DE | 29714564 | U1 | 10/1997 |
| DE | 10126100 | A1 | 12/2002 |
| DE | 10341055 | | 9/2004 |
| WO | 2007/100838 | A | 9/2007 |

OTHER PUBLICATIONS

International Search Report, ISA/EP, Rijswijk, NL, mailed Aug. 20, 2009.

International Preliminary Examination Report with annex and its translation.

* cited by examiner

COATING APPARATUS FOR COATING AN INSIDE OF A HOLLOW BODY WITH AN ATOMIZED FLUID

CROSS-REFERENCE TO RELATED APPLICATIONS

This application is a 371 U.S. National Stage of International Application No. PCT/EP2009/004386, filed Jun. 18, 2009. This application claims priority to German Patent Application No. 10 2008 030 272.4, filed Jun. 19, 2008. The disclosures of the above applications are entirely incorporated by reference herein.

The invention relates to a coating device according to the preamble of claim 1.

Coating devices of this type are known. Hollow bodies are often coated on their inside with an atomized fluid, in that the hollow body is held with an opening over an atomizing nozzle. The atomizing nozzle atomizes the fluid and thus generates an aerosol, that is, a mixture of propellant gas, for example, air, and suspended particles or fluid droplets formed from the fluid. This aerosol is blown in through the opening into the hollow body, whereupon the fluid droplets contained therein can settle on the inside of the hollow body. The atomization of the fluid through the nozzle is thereby of decisive importance for a uniform distribution of the fluid droplets on the inside of the hollow body, which is often unsuccessful.

It is therefore the object of the invention to create a coating device with the features cited in the preamble of claim 1, which renders possible a uniform distribution of the atomized fluid on the inside of the hollow body, in particular by an improved atomization of the fluid.

To attain this object a coating device is proposed which has the features cited in claim 1. It is characterized by at least one atomizing tube enclosing an atomizing channel, in which atomizing tube pressurized propellant gas for atomizing an unatomized fluid can be introduced and which has at least one outlet opening. It comprises at least one hollow needle having a discharge opening for the unatomized fluid, which interacts with the atomizing channel and is arranged essentially coaxially thereto, wherein the atomizing tube and the hollow needle form a Venturi arrangement. Propellant gas acted on with a pressure is thus introduced into the atomizing tube or the atomizing channel arranged therein. The unatomized fluid is introduced via a hollow needle, which interacts with the atomizing channel. This means that the unatomized fluid is atomized by means of an interaction of the atomizing channel and the hollow needle. This is essentially achieved by the propellant gas flowing through the atomizing tube or the atomizing channel. Any desired volume ratio of unatomized fluid to propellant gas can be provided thereby, however, preferably more propellant gas than fluid is introduced into the coating device.

The unatomized fluid exits through the discharge opening of the hollow needle. The discharge opening is arranged such that the fluid can be atomized by the interaction of the hollow needle and atomizing channel. The hollow needle is arranged essentially coaxially to the atomizing channel. The coating device can therefore be constructed to be extremely slim and in particular to have a narrow cross section. Through the atomization of the fluid an aerosol, that is, a mixture of the propellant gas and the atomized fluid or the fluid droplets, is present. The aerosol flows through the atomizing tube until it reaches the discharge opening and can exit from the atomizing tube. The discharge opening of the atomizing tube is arranged such that a very uniform distribution of the atomized fluid is ensured on the inside of the hollow body.

The coating arrangement is characterized in that the atomizing tube and the hollow needle form a Venturi arrangement. That means that this is an arrangement according to a Venturi nozzle or a Venturi tube. The discharge opening of the hollow needle is therefore arranged in a region with a narrowest cross section of the atomizing tube, or the hollow needle forms this narrowest cross section jointly with the atomizing tube. The cited cross section can thereby also form only one region of the narrowest cross section or can be a locally narrowest cross section or a region thereof. This does not mean that the region of the Venturi arrangement in total must form the narrowest cross section, in particular of the atomizing tube.

In the region of the Venturi arrangement there is a high flow rate of the propellant gas. The propellant gas stream tears the unatomized fluid out of the hollow needle through the discharge opening, there is therefore a momentum exchange between propellant gas and unatomized fluid. The unatomized fluid is accelerated thereby. Due to the acceleration and thus higher speed an underpressure is produced that exerts a suction effect on the unatomized fluid. A discharge pressure that is necessary to convey the unatomized fluid through the hollow needle can therefore be lower than the pressure pre sent in the region of the Venturi arrangement. Adjoining the Venturi arrangement, that is, downstream in the flow direction of the aerosol, the fluid can be further slowed down, for example, by a cross-sectional expansion. It is provided that there is a continuous flow of the propellant gas in the atomizing channel or the atomizing tube and a continuous flow of the unatomized fluid is introduced through the hollow needle. If the atomized fluid mixed with the propellant, that is, the aerosol, exits through the discharge opening of the atomizing tube downstream of the Venturi arrangement, the aerosol is decompressed to ambient pressure. While the decompression process is underway, a very high flow rate of the aerosol can be achieved in the region of the outlet opening. In particular, the fluid particles of the atomized fluid can be accelerated up to the supersonic range. With the coating device according to the invention a very good mixture of propellant gas and atomized fluid, in particular very small fluid droplets, can be achieved. A clearly improved homogeneity of the distribution of the fluid droplets on the inside of the hollow body can be achieved in connection with the very high exit velocity of the aerosol during an exit from the outlet opening.

A further development of the invention provides that the hollow needle at least in some regions is arranged in the atomizing channel. This means that the hollow needle runs in part in the atomizing channel or through the atomizing tube. The discharge opening of the hollow needle can likewise be provided in the atomizing channel. In this case, the Venturi arrangement is realized in the atomizing channel. It can also be provided that the hollow needle runs inside the atomizing channel, but the Venturi arrangement is not provided in the atomizing channel. Preferably, the hollow needle runs centrally in the atomizing channel.

A further development of the invention provides that a tapering of the atomizing channel is provided. The atomizing channel thus has a reduction of its inner cross section. The tapering can be provided, for example, to accelerate the propellant gas in the region of the Venturi arrangement or upstream thereof and thus to reduce the static pressure. In this case the tapering forms a part of the Venturi arrangement, in that it forms the narrowest cross section at least in some regions. Several taperings can also be provided, in particular an overall tapering of the atomizing channel can be carried out over several sections.

A further development of the invention provides that the discharge opening of the hollow needle is arranged in a region of the tapering. The discharge opening can thereby be arranged in the region upstream as well as downstream of the tapering. Preferably, the atomizing tube and the discharge opening of the hollow needle arranged in the region of the tapering form the Venturi arrangement.

A further development of the invention provides that the discharge opening is provided in a region of the outlet opening. The discharge opening is thus arranged in the region which—based on a total length of the atomizing tube or the atomizing channel—lies near to the outlet opening. In this manner the high flow rate of the aerosol in the region of the Venturi arrangement can be used to carry out the coating of the inside of the hollow body with the atomized fluid. In particular, therefore, no further structural measures need to be taken to increase the flow rate of the aerosol further. Instead, it can be provided to provide a diffuser downstream of the Venturi arrangements, which diffuser ensures a retardation of the flow rate, but also an even more effective atomization of the fluid.

A further development of the invention provides that the at least one outlet opening is provided on the front of the atomizing tube. This means that the outlet opening is embodied in the region of the coating device situated furthest downstream. The outlet opening fluidically connects the atomizing channel to the environment. Propellant gas and/or aerosol flowing through the atomizing tube or the atomizing channel can thus exit through the outlet opening. Preferably, the aerosol or the atomized fluid exits through the outlet opening essentially in the axial direction of the atomizing tube or in an exit cone arranged axially thereto.

A further development of the invention provides that the at least one outlet opening is provided in an outer wall of the atomizing tube. The aerosol can thereby exit in the radial direction of the atomizing tube. However, the aerosol can also exit at an angle to the radial direction.

A further development of the invention provides that at least two outlet openings are provided, which are provided in the outer wall of the atomizing tube and which are arranged distributed over a circumference of the atomizing tube, in particular lying diametrically opposite one another. The distribution of the aerosol exiting through the outlet openings on the inside of the hollow body can be influenced by a distribution of the outlet openings over the circumference of the atomizing tube. For example, larger or smaller quantities of the aerosol can be provided in regions of the inside for the coating.

For this purpose the outlet openings can be distributed irregularly over the circumference of the atomizing tube. A uniform, in particular diametrically opposite, arrangement of the outlet openings is also possible. For example, it can be provided to improve the uniformity of the coating of the inside of the hollow body via a sufficiently high number of outlet openings.

A further development of the invention provides that the at least one outlet opening can be displaced over at least a part of an axial extension of the inside of the hollow body by means of a displacement device. The outlet opening can thus be arranged at different positions inside the hollow body. This means in particular that the coating device or the atomizing tube are inserted at least in some parts into the hollow body. It is preferably provided that the outlet opening is displaced inside the hollow body during the coating process. A displacement into the hollow body or out of the hollow body is thereby possible. In the latter case, the outlet opening is initially placed in an axial position inside the hollow body which faces away from the opening of the hollow body through which an insertion of at least a part of the atomizing tube into the hollow body takes place. Subsequently, the coating of the inside is started, and during the coating process the outlet opening is displaced towards the opening of the hollow body. Preferably, a displacement of the outlet opening during the coating process takes place at a uniform speed.

In the displacement the outlet opening of the atomizing tube in a large region has the same spacing from the inside of the hollow body during the coating process. Thus a particularly uniform coating of the inside of the hollow body can be achieved. The displacement of the outlet opening can be achieved, for example, through a displacement of the atomizing tube with respect to the hollow body or through a displacement of the hollow body with respect to the atomizing tube. In order to be able to introduce the outlet opening even in slim hollow bodies, it is necessary that the coating device or the part of the coating device that is inserted into the hollow body, for example, the atomizing tube, has a small cross section. This is achieved, as described above, through the use of the Venturi arrangement, since this realizes the function necessary for coating the inside of the hollow body in a very small space. Due to the high exit velocity of the aerosol out of the outlet opening achieved by means of the Venturi arrangement, a displacement of the outlet opening is not necessary over an entire region of the inside of the hollow body to be coated. Preferably, the region in which a displacement of the outlet opening takes place is adjusted to the region to be coated of the inside of the hollow body and an atomization characteristic of the coating device. Atomization characteristic can mean, for example, the exit velocity and/or a characteristic size of the fluid droplets of the atomized fluid. Properties of the fluid used for coating are also to be included in this consideration, for example, the viscosity thereof.

A further development of the invention provides that the hollow body is held by a holding device during the coating. The hollow body is, for example, gripped by the holding device before the coating or inserted into the holding device. In this manner a stable, in particular vibration-free, holding of the hollow body during the coating is ensured. The hollow body is held by the holding device during the coating and after the coating process is removed therefrom or released by the holding device. Preferably, the holding device can be embodied in a clamp-shaped manner. This means that the hollow body is enveloped by the holding device at least in some regions while it is held thereby.

A further development of the invention provides that the hollow body can be clipped into the holding device or is held therein by clipping action. Preferably, it is provided that the hollow body can be clipped into an elastic region of the holding device therein. This means that the hollow body is pressed into the holding device, wherein an elastically embodied region of the holding device yields. If the hollow body is positioned in the holding device, due to its elastic embodiment the deformed region moves at least essentially back into its original position again, whereby the hollow body is clipped into the holding device. Through the described clipping effect, the hollow body is held in the holding device firmly, in particular not displaceable axially and/or radially, (with respect to the holding device). The holding of the hollow body in the holding device by clipping effect makes it possible to embody the holding device without mechanically moving parts and thus extremely cost-effectively. Alternatively, the clipping effect can be achieved by means of spring force on a region of the holding device supported in a moveable, in particular, pivotable manner.

A further development of the invention provides that the hollow body is held by means of the holding device in a pivoting and/or displaceable manner. The hollow body is thereby in particular displaceable laterally, that is, in a plane perpendicular to a vertical axis of the holding device. Uncoupled from a later displaceability, a displacement of the hollow body in the vertical direction, that is, parallel to the vertical axis of the holding device, can also be provided. For example, the hollow body can be moved or displaced relative to the outlet opening of the atomizing tube via the vertical displacement of the hollow body by means of the holding device. The holding device also permits a swivel motion of the hollow body, in particular about the vertical axis of the holding device. It can be provided to permit only a swivel motion or a rotary motion of the holding device about the vertical axis, while a swivel motion or a rotary motion about further axes is prevented by the holding device.

A further development of the invention provides that the atomizing tube can be centered by means of a centering device with regard to a longitudinal axis of the hollow body therein. In order to ensure the most uniform possible distribution of the atomized fluid on the inside of the hollow body, a constant spacing of the atomizing tube or the outlet opening thereof from the inside of the hollow body must be ensured. This means in particular that a spacing in the radial direction from the outlet opening to the inside of the hollow body over a circumference of the inside must be essentially the same. The centering device ensures that the atomizing tube is arranged in the center with respect to the longitudinal axis of the hollow body. A centering can be achieved either via a centering of the atomizing tube with respect to the hollow body or via an alignment of the hollow body relative to the atomizing tube. Thus either a displacement of the atomizing tube or of the hollow body takes place in order to achieve a central arrangement of the atomizing tube with respect to the longitudinal axis of the hollow body. The centering preferably takes place with mechanical means, but can also be carried out by means of a control or regulating device connected to sensors, which can displace the atomizing tube and/or the hollow body via actuators.

A further development of the invention provides that the longitudinal axis of the hollow body is aligned, in particular in an axially parallel manner, with respect to a centering axis of the centering device by the holding device. The holding device can thus be used to displace or to pivot the hollow body relative to the centering device. Preferably, the holding device is used to convey the hollow body to the centering device. It is in particular provided thereby that the longitudinal axis of the hollow body is aligned in an axially parallel manner to the centering axis of the centering device. It is achieved thereby that a constant spacing of the outlet opening or the atomizing tube from the inside of the hollow body is ensured during a displacement of the outlet opening in the hollow body. Alternatively, the centering device can also be displaced with respect to the holding device, so that the described alignment is achieved.

A further development of the invention provides that the displacement device is provided on the centering device. This means that the displacement device and the centering device form one unit. This further development has the advantage that an accidental displacement of the centering device with respect to the displacement device cannot occur, since preferably a mechanical connection is embodied between the displacement device and the centering device.

A further development of the invention provides that the centering device comprises at least one centering element, which has an essentially frustoconical or conical outer circumference. The at least one centering element defines at least in some regions the outer circumference of the centering device. The outer circumference is used to center the hollow body. Preferably, the centering elements form an essentially frustoconical or conical outer circumference. To this end the centering elements can have a shape tilted in the radial direction. The centering elements do not need to form the region of the outer circumference of the centering device that is used for centering the hollow body in circumferentially continuous manner. For example, it can be provided that the centering elements project from a surface of the centering device and thus define the outer circumference. In the embodiment of the essentially frustoconical or conical outer circumference it is not necessary that the centering elements also form a base surface or a cover surface of the truncated cone or the cone. It can instead be provided that the centering elements are provided only in one region of the circumferential surface of the truncated cone or of the cone.

A further development of the invention provides that at least two, preferably three, centering elements are provided, which are embodied as centering arms distributed over the circumference of the centering device. The centering arms overlap, for example, in the radial direction a radial cross section of the centering device at least in some regions. Preferably, the centering arms or the centering elements have inclined planes on which the hollow body is supported and thus can be centered. The centering arms are thereby preferably uniformly distributed over the circumference of the centering device in order to achieve an exact centering of the hollow body with respect to the centering device. For the same reason preferably three centering elements are provided.

A further development of the invention provides that the centering device lies essentially outside a flow of atomized fluid exiting from the outlet opening. This means that the centering device is arranged with respect to the atomizing tube such that the fluid flow exiting from the outlet opening, that is, a flow of aerosol, cannot impinge the centering device. The distribution of the aerosol on the inside of the hollow body is thus not impaired. Possibly (atomized) fluid can come into contact with the centering device, but not directly after an exit from the outlet opening or directly before an impingement of the atomized fluid on the inside of the hollow body.

A further development of the invention provides that the atomizing tube has a length that corresponds essentially to the axial extension of the hollow body. In order to be able to achieve a uniform coating of as large an area as possible of the inside of the hollow body, the outlet opening is preferably displaceable over as large an area of the hollow body as possible. For this purpose the atomizing tube has approximately the same length as the hollow body, in particular an axial extension of a region to be coated of the inside of the hollow body.

A further development of the invention provides that the propellant gas is air or nitrogen. Both gases are easy to handle. Moreover, because they are available in large quantities, they are low-priced.

A further development of the invention provides that the fluid is a polymer, in particular silicone oil, or has a polymer. In addition to a polymer, alternatively an emulsion can be used in which a polymer is contained, for example, a silicone oil emulsion.

A further development of the invention provides that the hollow body is a syringe or a carpule. Particularly preferably, the coating device can thus be used for syringes and/or carpules. Both have a small diameter compared to their length. It is therefore difficult on the one hand to achieve a uniform coating of the inside by blowing an aerosol through an opening of the hollow body and on the other hand to displace the coating device in the hollow body due to the small diameter of the hollow body. These problems are solved by the coating device described above. Through the use of a Venturi arrangement, the coating device can be realized with a minimal space requirement whereby the displacement of the coating device or the atomizing tube in the hollow body and thus a uniform coating of the inside of the hollow body is possible.

A further development of the invention provides that the hollow body is made of glass.

Figure 2:
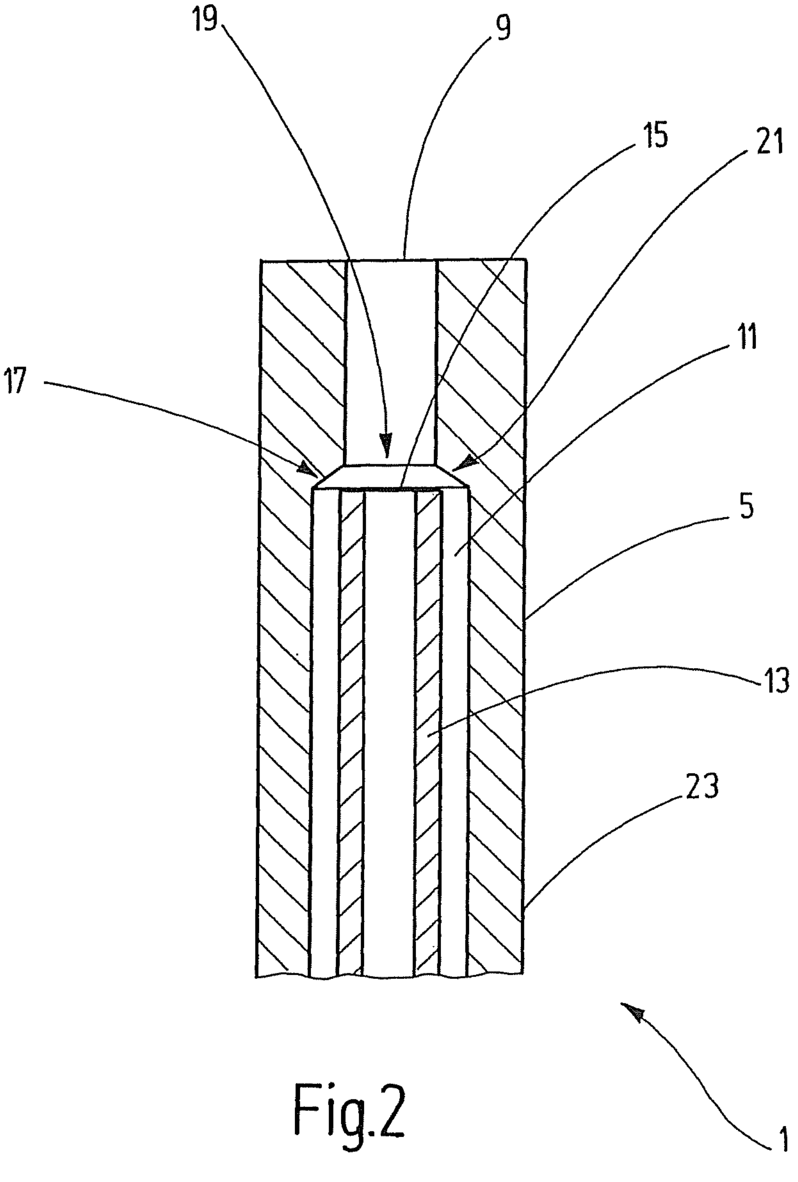
Figure 3A:
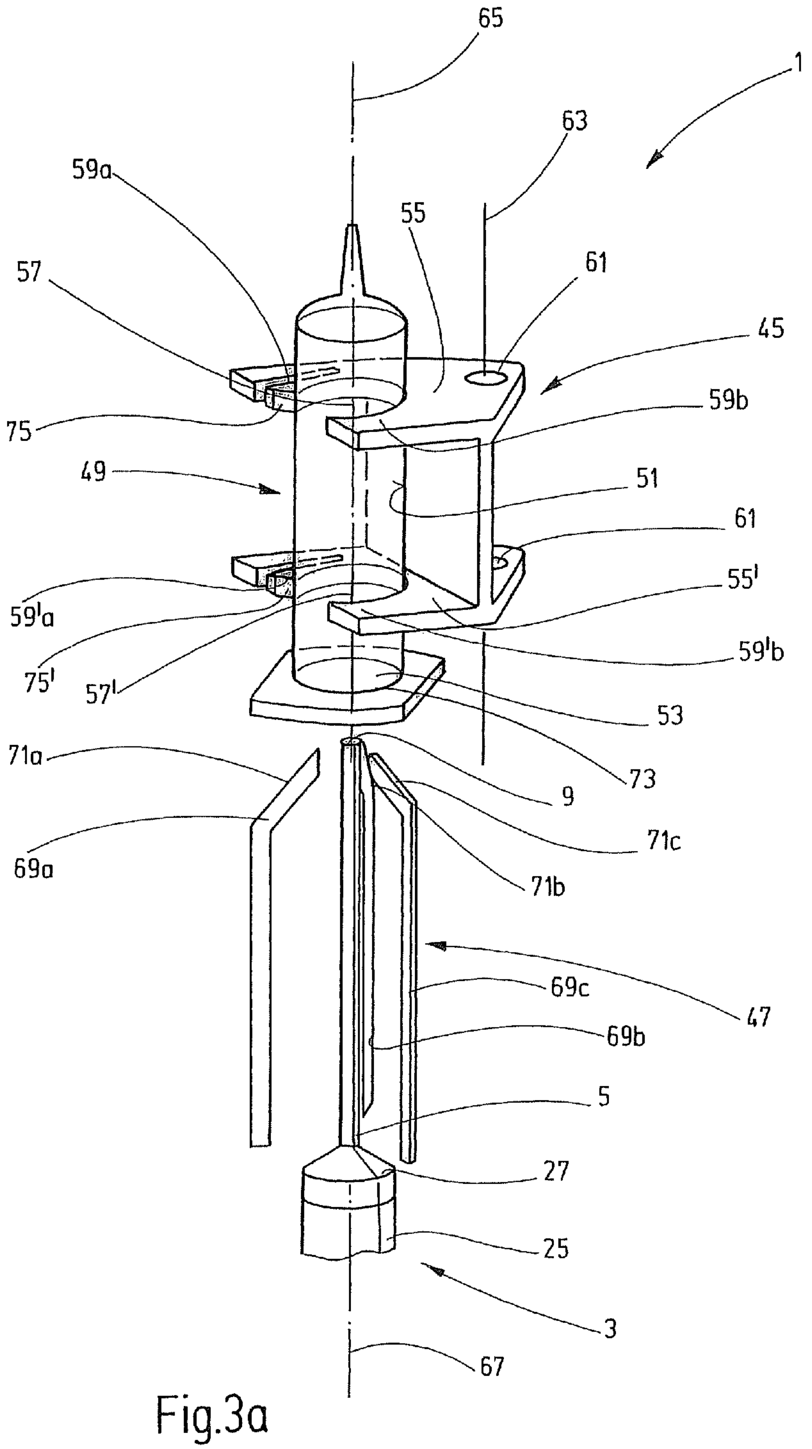
Figure 3B:
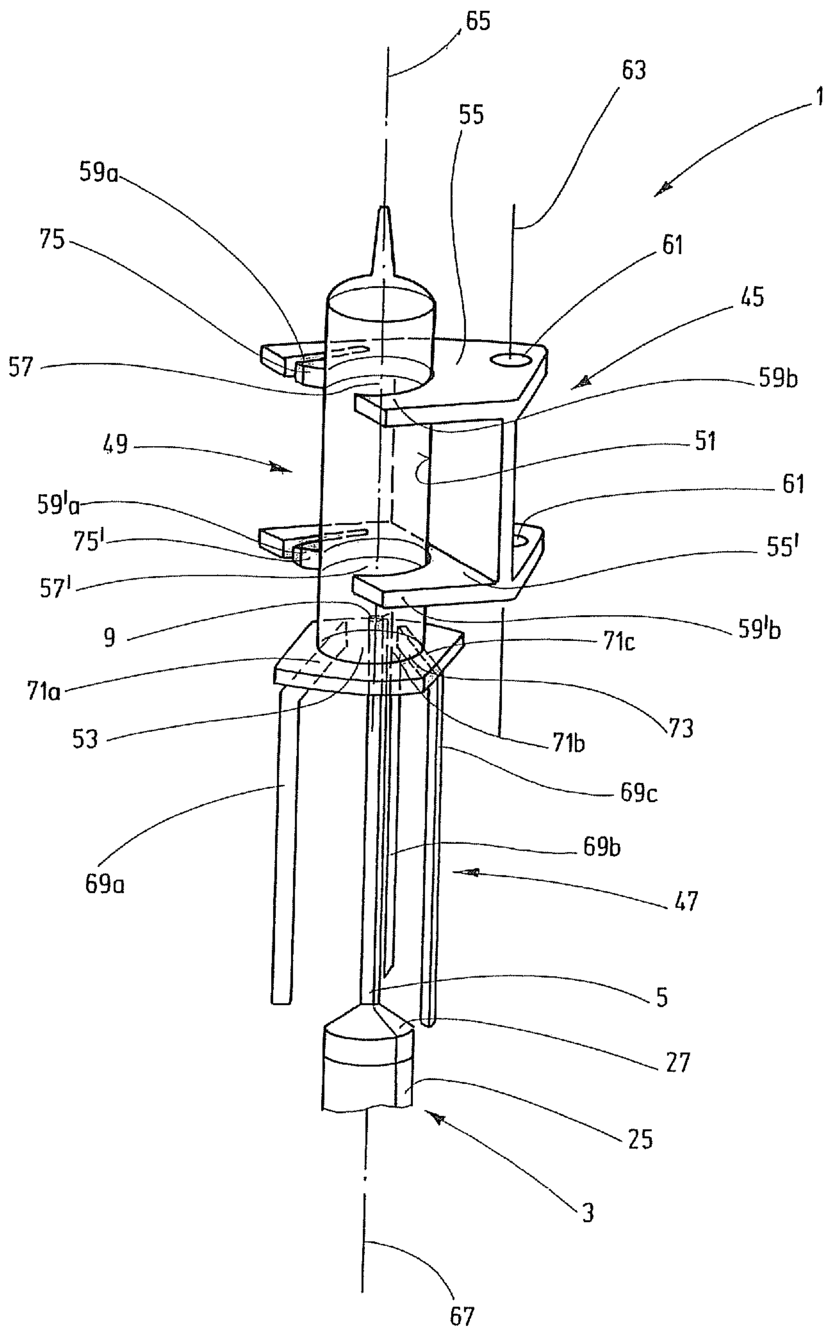
Figure 3C:
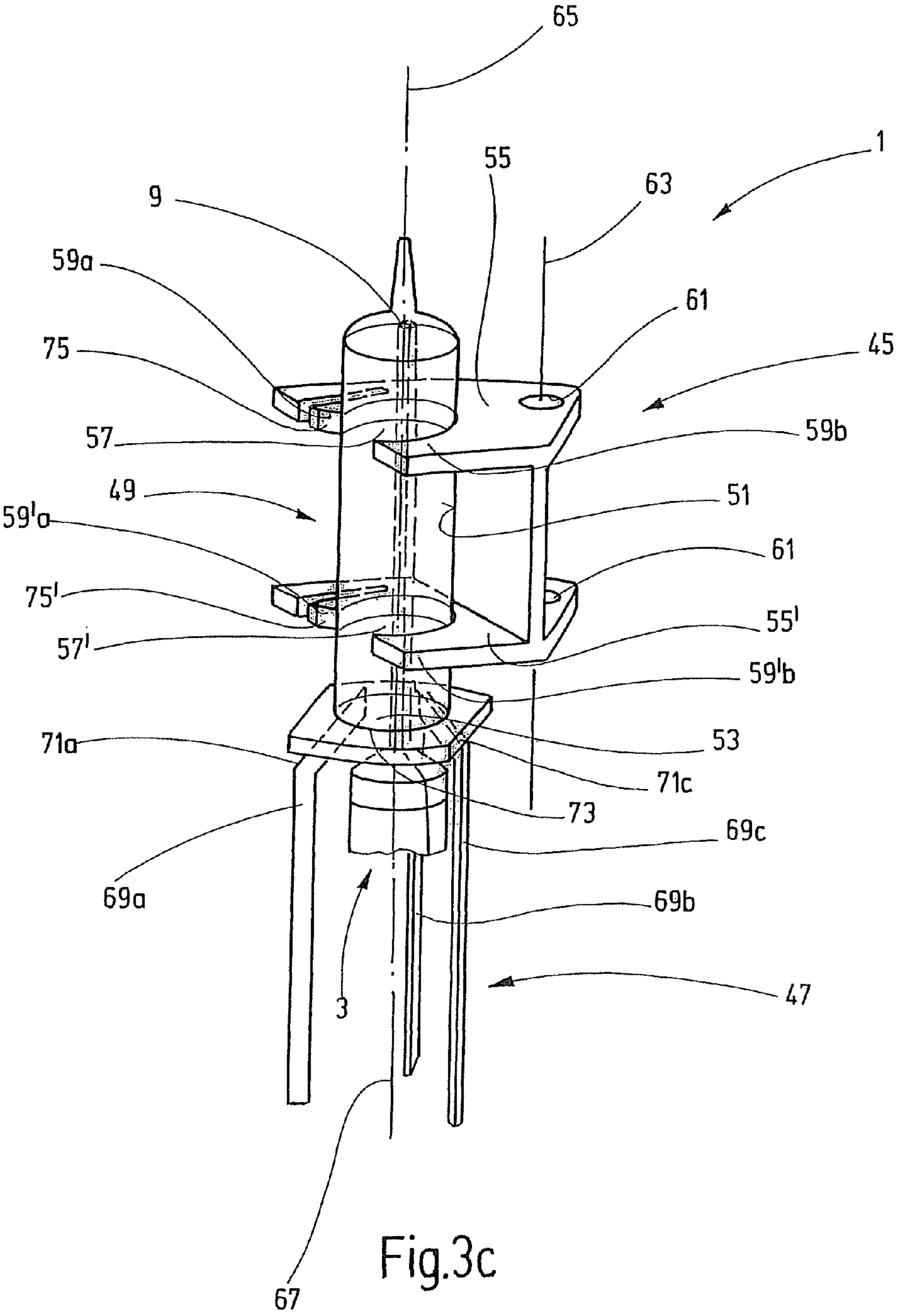

The invention is explained in more detail below based on the drawing. They show:

FIG. 1 A cross section through the coating device,

FIG. 2 A detailed view of the coating device in the region of an outlet opening, FIG. 3*a* The coating device and a hollow body to be coated before a centering and a coating process, FIG. 3*b* The coating device and the hollow body during the centering process, and FIG. 3*c* The coating device with an atomizing tube displaced in the hollow body after the centering process and before the coating process.

FIG. 1 shows a coating device 1 that has a base element 3 and an atomizing tube 5. The atomizing tube 5 has an inlet opening 7 as well as an outlet opening 9 for an atomized fluid or aerosol. In the example shown the inlet opening 7 as well as the outlet opening 9 are arranged at the ends of the atomizing tube 5. The inlet opening 7 and the outlet opening 9 of the atomizing tube 5 are fluidically coupled by means of an atomizing channel 11, which runs inside the atomizing tube 5. This means that fluid entering into the atomizing tube 5 through the inlet opening 7 flows through the atomizing channel 11 in order to exit out of the outlet opening 9 on the side of the atomizing tube 5 far from the inlet opening 7. A hollow needle 13 runs, at least in some regions, in the interior of the atomizing channel 11, which hollow needle is arranged coaxially to the atomizing channel 11. The hollow needle 13 has a front discharge opening 15, which is provided in the region of the outlet opening 9. The supply of the coating device 1 with an unatomized fluid is ensured by means of the hollow needle 13. In the region of the discharge opening 15, the atomizing tube 5 or the atomizing channel 11 arranged therein has a tapering 17, in the region of which an inner cross section of the atomizing channel 11 is reduced up to the outlet opening 9. The tapering 17 and the discharge opening 15 of the hollow needle 13 are positioned with respect to one another such that the atomizing tube 5 and the hollow needle 13 form a Venturi arrangement 19. The Venturi arrangement 19 designates an arrangement in which the discharge opening 15 for the unatomized fluid is arranged in a region 21 that has a locally smallest cross section of the atomizing channel 11. In the example shown in FIG. 1, the hollow needle 13 jointly with the tapering 17 forms the region 21, that is, an outer diameter of the hollow needle 13 reduces the cross section of the atomizing channel 11 in connection with the tapering 17 to the locally smallest cross section. The discharge opening 15 also lies in the region 21.

Alternatively to the arrangement of the outlet opening 9 on the front on the atomizing tube 5, at least one outlet opening 9 can be provided in an outer wall 23 of the atomizing tube 5 (not shown). For example, at least two outlet openings 9 can be provided in the outer wall 23, wherein in a preferred embodiment respectively two outlet openings 9 lie diametrically opposite one another. However, more than two—preferably uniformly—over the circumference of the outer wall 23 are also possible.

The base element 3 of the coating device 1 has a connecting member 25 and a screw-in element 27 holding the atomizing tube 5. The atomizing tube 5 is thereby held in a bore provided in the longitudinal direction of the screw-in element 27. This can be realized, for example, in that the screw-in element 27 is embodied as a clamping member, which by screwing into a thread 31 of the connecting member 25 exerts a clamping effect or a squeezing effect on the atomizing tube 5 and thus fixes it. Two pipe connections 33 and 35 are provided on the connecting member 25. A connection of the coating device 1 to a propellant gas supply (not shown) is produced via the pipe connection 33, while the unatomized fluid can be fed via the pipe connection 35. The pipe connection 33 is in fluidic communication with a collecting chamber 37, which is used as a settling chamber for settling the propellant gas before this enters the atomizing tube 5 via the inlet opening 7 connected to the collecting chamber 37. The pipe connection 35 is connected to a collecting chamber 39, via which a connection to the hollow needle 13 is established. The collecting chambers 37 and 39 are separated from one another by a separating element embodied as a plug 41. This means that there is no fluid connection between the collecting chamber 37 and the collecting chamber 39, thus the propellant gas first cannot come into contact with the unatomized fluid. The coating device 1 furthermore has a holding device 43, which is provided on the connecting member and is used for attachment to a further component (not shown).

FIG. 2 shows a detailed view of the coating device 1 in the region of the outlet opening 9 or of the Venturi arrangement 19. It is clear that the Venturi arrangement 19 is arranged in the region of the outlet opening 9. This means that the Venturi arrangement 19 is arranged near to the outlet opening 9 with respect to a length of the atomizing tube 5. In the region of the atomizing tube 5 in which the hollow needle 13 is arranged, there is a cross section which can be flowed through by the propellant gas. In the region of the Venturi arrangement 19, that is, in the region in which the tapering 17 and the discharge opening 15 of the hollow needle 13 are arranged, there is a reduced cross section compared to the cited cross section located on the upstream side. The propellant gas is thus accelerated, whereupon the static pressure of the propellant gas drops. Further downstream the cross-sectional reduction of the atomizing channel 11 caused by the hollow needle 13 does not apply, whereby the cross section is expanded again. This means that the discharge opening 15 is arranged in the region of the smallest cross section. Only the locally smallest cross section is to be understood in terms of the narrowest cross section. It is definitely possible for the atomizing channel 11 away from the Venturi arrangement 19 to have an even smaller cross section. The arrangement of the discharge opening 15 in the region of the smallest cross section means that at this point there is a reduced pressure. This follows, for example, from Bernoulli's equation. Due to the low pressure the unatomized fluid can exit through the discharge opening 15 from the hollow needle 13, without a high pressure having to be impressed on the unatomized fluid. Due to the different cross sections there thus is a contraction of the atomizing channel 11 and a subsequent diffuser in the region of the Venturi arrangement 19, in the course of which the cross section is enlarged again. The Venturi arrangement 19 causes a fine atomization of the unatomized fluid by means of the propellant gas.

FIG. 3*a* shows the coating device 1, which, in addition to the atomizing tube 5 and the base element 3, has a holding device 45 and a centering device 47. A hollow body 49, in this example a syringe cylinder, is held in the holding device 45. The hollow body 49 has an inside 51 as well as an opening 53. In the example shown in FIG. 3*a*, the holding device 45 has two clamping bases 55, 55', which respectively have a cut-out 57, 57' which is surrounded at least in some regions by respectively two holding lugs 59*a*, 59*b*, 59'*a*, 59'*b*. The hollow body 49 is held in the cut-outs 57. Respectively one of the holding lugs 59*a*, 59*b*, 59'*a*, 59'*b* is embodied as an elastic holding lug and can deflect outwards in the radial direction with respect to the cut-out 57, 57' with force impingement. The elastic holding lugs 59*a*, 59*b*, 59'*a*, 59'*b* allow an insertion of the hollow body 49 into the cut-out 57, 57' and a subsequent holding of the hollow body 49. The two clamping bases 55, 55' are arranged spaced apart from one another in the vertical direction. The holding device 45 can be arranged by means of bores 61, for example, on pins (not shown) of an adjacent device (not shown). A longitudinal axis 63 of the holding device 45 runs centrally through the bores 61. It permits a free pivoting of the hollow body 49 about the longitudinal axis 63. Furthermore it is provided that the hollow body 49 can be displaced by means of the holding device 45 in the lateral direction, that is, in a plane perpendicular to the longitudinal axis 63. The holding device 45 holds the hollow body 49 such that a longitudinal axis 65 of the hollow body runs parallel to the longitudinal axis 63 of the holding device. It is also provided that the holding device 45 is arranged such that the longitudinal axis 63 of the holding device 45 as well as the longitudinal axis 65 of the hollow body run parallel to a centering axis 67 of the centering device 47.

The centering device 47 has three centering elements 69, which here are embodied as centering arms. The centering elements 69*a*, 69*b*, 69*c* are arranged such that they do not lie in any position inside a flow of atomized fluid exiting from the outlet opening 9 of the atomizing tube 5. This prevents the centering device 47 from influencing the flow of atomized fluid and thus a uniform coating of the inside 51 of the hollow body 49. The hollow body 49 can be arranged by means of the centering device 47 or the centering elements 69*a*, 69*b*, 69*c* such that the centering axis 47 and the longitudinal axis 65 of the hollow body 49 coincide. In this case the outlet opening 9 of the atomizing tube 5 is also positioned centrally with respect to the hollow body 49. The positioning of the hollow body 49 is carried out via inclined planes 71*a*, 71*b*, 71*c* of the centering elements 69. These run radially inwards and upwards with respect to the centering axis 67 and thus form a frustoconical or conical outer circumference of the centering device 47. In the example shown, the inclined planes 71*a*, 71*b*, 71*c* extend only in sections towards the centering axis 67 or the atomizing tube 5. Thus a frustoconical outer circumference of the centering device 47 is formed, but without a base surface or cover surface of the truncated cone. The extension of the inclined planes 71*a*, 71*b*, 71*c* inwards is carried out so far that the distance from ends of the centering elements 69*a*, 69*b*, 69*c* from one another is smaller than a diameter of the opening 53 of the hollow body 49. Thus during a centering process an edge 73 of the opening 53 of the hollow body 49 can come into bearing contact with the inclined planes 71*a*, 71*b*, 71*c* or the centering elements 69*a*, 69*b*, 69*c* of the centering device 47.

The function of the coating device 1 is described below based on FIGS. 3*a*, 3*b* and 3*c*. FIG. 3*a* shows the coating device 1 and the hollow body 49 to be coated before the centering process and the coating process. First the coating device 1 and the hollow body 49 are prepared, wherein the hollow body 49 is clipped into the cut-out 57. This is carried out in that the hollow body 49 is pressed into the region not enclosed by the holding lugs 59*a*, 59*b*, 59'*a*, 59'*b*. The hollow body 49 thus exerts a force via tilted surfaces 75, 75' in the radial direction on the holding lugs 59*a*, 59*b*, 59'*a*, 59'*b*, whereupon they yield and the hollow body 49 can be inserted into the cut-out 57, 57'. Through an elastic embodiment of the holding lugs 59*a*, 59*b*, 59'*a*, 59'*b* or through a spring action of a spring (not shown), the holding lugs 9 are brought back into their starting position again after the insertion of the hollow body 4. Thus the hollow body 49 is enclosed at least in some regions by the holding lugs 59*a*, 59*b*, 59'*a*, 59'*b* in the cut-out 57, 57' and is held therein by clip action. Thus the hollow body 49 is arranged such that its longitudinal axis 65 runs parallel to the longitudinal axis 63 of the holding device 45 as well as the centering axis 67 of the centering device 47. Consequently, the longitudinal axis 65 of the hollow body 49 is already arranged essentially parallel to the atomizing tube 5. In the condition shown in FIG. 3*a*, the coating device 1 is located in a starting position. This means that the atomizing tube 5 has not yet been displaced by means of a displacement device (not shown), but is arranged such that the outlet opening 9 is located approximately at the level of the maximum extension of the centering device 47 in the vertical direction. This means that the outlet opening 9 is not arranged above the centering device 47. The hollow body 49 is pivoted about the longitudinal axis 63 of the holding device 45 by the holding device 45.

The hollow body 49 is displaced below by means of the holding device 45 in the direction of the centering device 47, so that the longitudinal axis 65 of the hollow body 49 approximately coincides with the centering axis 67. Alternatively, the centering device 47 can also be displaced, without the holding device 45 being moved, so that the alignment described above is achieved. Subsequently, either the holding device 45 is lowered or the centering device 47 is raised. The condition shown in FIG. 3*b* is thus produced.

FIG. 3*b* shows the coating device 1 and the hollow body 49 during the centering process. Through the raising of the centering device 47 or the lowering of the holding device 45, the edge 73 of the hollow body comes into bearing contact with the inclined planes 71*a*, 71*b*, 71*c* of the centering device 47. Either the centering device 47 or the holding device 45 are moveable laterally, that is, displaceable in a plane perpendicular to the centering axis 67 or the longitudinal axis 63. The hollow body 49, as soon as it is placed on the centering elements 69*a*, 69*b*, 69*c*, due to the force of gravity or a force impressed by the holding device 45 in the vertical direction downwards or by the centering device 47 in the vertical direction upwards, can thus be aligned such that its longitudinal axis 65 coincides with the centering axis 67. The edge 73 thereby slides over the inclined planes 71*a*, 71*b*, 71*c* of the centering elements 69*a*, 69*b*, 69*c*.

As soon as all of the centering elements 69*a*, 69*b*, 69*c* are in planar contact with the edge 73, it can be assumed that the desired arrangement of the hollow body 49 has been produced. This means that the hollow body 49 is aligned such that its longitudinal axis 65 coincides with the centering axis 67 or a longitudinal axis of the atomizing tube 5. A distance from the outlet opening 9 to points of the inside 51 of the hollow body 49 arranged in a vertical plane is therefore the same for all of the points. In this manner a particularly homogeneous coating of the inside 51 can be achieved during a subsequent coating process. As soon as the centering process described based on FIG. 3*b* has been completed, the coating of the inside 51 of the hollow body 49 is carried out.

To this end, as shown in FIG. 3*c*, initially the atomizing tube 5 or the outlet opening 9 is displaced into the hollow body 59. Subsequently, the coating process is started, that is, propellant gas as well as unatomized fluid is introduced into the coating device 1. In the meantime, the outlet opening 9 is moved vertically downwards and the atomizing tube 5 is thus moved out of the hollow body 49. During the coating process or the removal of the atomizing tube 5 from the hollow body 49, the space from the outlet opening 9 is thus the same for a majority of the points on the inside 51.

Alternatively, it can also be provided that the coating process is carried out during the insertion of the atomizing tube 5 into the hollow body 49. That means that the atomizing tube 5 is not first displaced into the hollow body 49 and the coating is not applied until during the removal. Several coating passes are also possible. A coating can be carried out, for example, during the insertion of the atomizing tube 5 into the hollow body 49 as well as during the outward movement. During the coating process the holding device 45 and the centering device 47 are preferably fixed to one another. This also ensures a secure fixing of the hollow body 49 with respect to the atomizing tube 5 or the outlet opening 9. Following the coating process, the atomizing tube 5 is removed from the hollow body 49 and either the holding device 45 is moved upwards or the centering device 47 is moved downwards so that the hollow body 49 is no longer connected to the centering device 47. Subsequently, the hollow body 49 is removed from the holding device 45, again by impressing a force on the hollow body 49 in the direction of the region that is not enclosed by the holding lugs 59*a*, 59*b*, 59'*a*, 59'*b*. Subsequently, further processing steps can be carried out on the hollow body 49.

The invention claimed is:

1. A coating device for coating an inside of a hollow body with an atomized fluid, the coating device comprising:

at least one atomizing tube enclosing an atomizing channel in which propellant gas for atomizing an unatomized fluid is introduced and which has at least one outlet opening on the at least one atomizing tube having a tube discharge opening; and at least one hollow needle having a needle discharge opening for the unatomized fluid, the at least one hollow needle interacting with the atomizing channel and arranged essentially coaxially thereto, the at least one atomizing tube and the at least one hollow needle forming a Venturi arrangement having a narrowed cross section proximate the needle discharge opening of the at least one hollow needle, the needle discharge opening of the at least one hollow needle arranged essentially coaxially to the atomizing channel, the tube discharge opening of the at least one atomizing tube arranged downstream of the Venturi arrangement; and wherein the at least one outlet opening is displaceable over at least a part of an axial extension of the inside of the hollow body and the at least one atomizing tube is centered by a centering device with regard to a longitudinal axis of the hollow body;

wherein the needle discharge opening is located in a region of the at least one atomizing tube having a narrowest cross section;

wherein the hollow body is a syringe or a carpule; and wherein the centering device includes a plurality of centering arms, each centering arm having a first segment and a second segment, each first segment extending axially with respect to a centering axis of the centering device, each second segment defining an inclined plane extending radially and axially relative to the centering axis and for engaging an interior of the hollow body, the at least one atomizing tube being axially movable relative to the plurality of centering arms.

2. The coating device according to claim 1, wherein the at least one hollow needle is arranged at least in some regions in the atomizing channel.

3. The coating device according to claim 1, wherein the atomizing channel includes a tapering.

4. The coating device according to claim 3, wherein the needle discharge opening of the at least one hollow needle is arranged in a region of the tapering.

5. The coating device according to claim 1, wherein the needle discharge opening is provided in a region of the at least one outlet opening.

6. The coating device according to claim 1, wherein the at least one outlet opening is provided on a front of the at least one atomizing tube.

7. The coating device according to claim 1, wherein the at least one outlet opening is provided in an outer wall of the at least one atomizing tube.

8. The coating device according to claim 1, wherein the hollow body is held by a clamp-shaped holding device during the coating.

9. The coating device according to claim 8, wherein the hollow body is clipped into the holding device or is held therein by clipping action.

10. The coating device according to claim 8, wherein the hollow body is held by the holding device in a pivoting and/or displaceable manner.

11. The coating device according to claim 8, wherein the longitudinal axis of the hollow body is aligned, in particular in an axially parallel manner, to the centering axis of the centering device by the holding device.

12. The coating device according to claim 1, wherein a displacement device is provided on the centering device.

13. The coating device according to claim 1, wherein the centering device forms an essentially frustoconical or conical outer circumference.

14. The coating device according to claim 1, centering arms of the plurality of centering arms are distributed over a circumference of the centering device.

15. The coating device according to claim 14, wherein the plurality of centering arms includes three centering elements.

16. The coating device according to claim 1, wherein the centering device lies essentially outside a flow of atomized fluid exiting from the at least one outlet opening.

17. The coating device according to claim 1, the at at one atomizing tube has a length that corresponds essentially to the axial extension of the hollow body.

18. The coating device according to claim 1, wherein the propellant gas is air or nitrogen.

19. The coating device according to claim 1, wherein the fluid is a polymer.

20. The coating device according to claim 1, wherein the hollow body is made of glass.

21. The coating device according to claim 1, wherein a diameter of the atomizing channel tapers proximate the hollow needle discharge opening in a direction toward the atomizing tube discharge opening.

22. The coating device according to claim 1, wherein the at least one atomizing tube has a first end adapted to be in fluid communication with a first collection chamber and a second end defining the discharge opening, and wherein the at least one hollow needle is adapted to be in fluid communication with a second collection chamber.

23. The coating device according to claim 1, wherein the atomizing channel has a first portion with a first diameter and a second portion with a second diameter, the first diameter being greater than the second diameter, the atomizing channel further including an intermediate portion tapering from the first portion to the second portion, the needle discharge opening proximate a first intersection between the first portion and the intermediate portion and spaced upstream from a second intersection between the intermediate portion and the second portion.

24. The coating device of claim 1, wherein the first segments cooperate to define a conical outer surface of the centering device and the second segments cooperate to define an outer frustoconical surface of the centering device.

25. The coating device of claim 1, wherein each second segment includes a free end, the free ends spaced apart from one another.

26. The coating device of claim 24, wherein the conical outer surface has a diameter greater than a diameter of the hollow body.

27. The coating device of claim 26, wherein the frustoconical outer surface has a first frustoconical diameter greater than the diameter of the hollow body and tapers to a second frustoconical diameter less than the diameter of the hollow body.

* * * * *